(12) United States Patent
Spaide

(10) Patent No.: US 7,670,001 B2
(45) Date of Patent: Mar. 2, 2010

(54) REFLECTANCE MEASUREMENT OF MACULAR PIGMENT USING MULTISPECTRAL IMAGING

(76) Inventor: Richard Spaide, 530 E. 72nd St., Apt. 15E, New York, NY (US) 10021

( * ) Notice: Subject to any disclaimer, the term of this patent is extended or adjusted under 35 U.S.C. 154(b) by 0 days.

(21) Appl. No.: 11/750,164

(22) Filed: May 17, 2007

(65) Prior Publication Data

US 2008/0266520 A1    Oct. 30, 2008

Related U.S. Application Data

(60) Provisional application No. 60/913,885, filed on Apr. 25, 2007, provisional application No. 60/926,345, filed on Apr. 26, 2007.

(51) Int. Cl.
*A61B 3/00* (2006.01)
*A61B 3/08* (2006.01)
*A61B 3/10* (2006.01)

(52) U.S. Cl. .................. 351/200; 351/202; 351/213

(58) Field of Classification Search .............. 351/200, 351/202, 205, 210, 213, 216, 221, 222, 233
See application file for complete search history.

(56) References Cited

U.S. PATENT DOCUMENTS 7,039,452 B2 *  5/2006  McClane et al. ............ 600/424

* cited by examiner

*Primary Examiner*—Jessica T Stultz
*Assistant Examiner*—Brandi N Thomas
(74) *Attorney, Agent, or Firm*—Ronald Abramson; Hughes Hubbard & Reed LLP

(57) ABSTRACT

Methods and apparatus are provided for accurately imaging, assessing and measuring a patient's macular pigment. A multiband filter is employed in combination with a color digital fundus camera to provide a method that operates with a single imaging exposure. The multiband filter has bandpass regions within spectral ranges of the red, green and blue detectors of the CCD array employed within the fundus camera, the bandpass regions being sufficiently sharply defined so as to avoid regions where the CCD detector responses spectrally overlap. This provides three discrete channels of grayscale data corresponding to the bandpass regions of the multiband filter, which can be used to calculate macular pigment topographically. Methods are also disclosed for calculating the optical density of the macular pigment and advantageously displaying the resulting data.

23 Claims, 7 Drawing Sheets

1A  1B  1C

REFLECTANCE MEASUREMENT OF MACULAR PIGMENT USING MULTISPECTRAL IMAGING

CROSS-REFERENCE TO RELATED APPLICATIONS

This application claims the benefit of the filing date of my U.S. Provisional Patent Applications each entitled "Reflectance Measurement of Macular Pigment Using Multispectral Imaging, Ser. Nos. 60/913,885, filed Apr. 25, 2007, and 60/926,354, filed Apr. 26, 2007, which are each incorporated herein by reference, and further incorporates herein by reference my U.S. patent application entitled "Autofluorescence Photography Using a Fundus Camera," Ser. No. 11/742,672 filed on May 1, 2007.

BACKGROUND OF THE INVENTION

1. Field of the Invention

The present invention is in the field of opthalmology, and more particularly concerns measuring macular pigment by imaging the macula with a plurality of wavelengths simultaneously.

2. Background of the Related Art

There are a number of circumstances that arise in opthalmology in which it is necessary or desirable to measure macular pigment. Increased ingestion of lutein and zeaxanthine has been associated with increased risk of macular degeneration in some studies.[3] (All bibliographic references are listed by number in Table I.) Supplements to increase the amounts of these pigments are a popular means to try to decrease the risk of macular degeneration. The absorption of these pigments appears to vary from individual to individual.[4,5] Some studies suggest a correlation between serum levels of lutein and zeaxanthine and reduced risk, while others do not.[6-8] However, the relationship between blood levels of these pigments and ultimate deposition in the macula is not known with certainty. In some circumstances there appears to be increased metabolism of macular pigments. Smoking, for example, is associated with decreased levels of macular pigment.[9] Obesity is also associated with decreased pigment,[10] perhaps because these pigments are fat soluble.

Having a method to measure macular pigment would help in evaluating and treating older patients at risk for macular degeneration. There are several ways to measure macular pigment. Heterochromatic flicker matching is a psychophysical test where the person has to adjust the brightness of colors so that they match. This is difficult for some patients to do, particularly as they get older. This test measures only one point in the macula, the one used to visualize the colors. The tester does not know what point is being measured. It is likely that the distribution of macular pigments in the macula is important, not just the amount at the one point being measured. Raman spectroscopy, another measurement method, uses inelastic scattering of the macular pigments to measure their presence. Raman spectroscopy measures one point in the eye and the exact location of this point is not known to the tester.

Additional methods used to measure the amount of macular pigment usually use more than one wavelength. Reflectance photography uses two wavelengths. The first wavelength is blue, in the region of maximal absorbance of the macular pigment, which is around 465 nm. The second wavelength chosen is to be somewhat longer, but out of the range of maximal absorption of the macular pigment, which declines to low levels at wavelengths longer than 530 nm. The ratio of the optical absorption at the two test wavelengths can be used to calculate the optical density.

Autofluorescence photographic approaches also can use two wavelengths to estimate the amount of macular pigment present. In this method two wavelengths are used to stimulate autofluorescence, one blue and another that is usually in the green portion of the spectrum. The blue light would be blocked by the macular pigment while the green light would not. The ratio of the induced autofluorescence would be indicative of the amount of macular pigment.

There are advantages to both the reflectance photography and autofluorescence methods. The reflectance method does not rely on the unproven assumption that the difference in the amount of fluorescence caused by the two wavelengths is only due to the presence of blue light absorbing pigments. Reflectance methods may, however, contain artifactual errors in that the surface of the retina may reflect light in inverse proportion to the wavelength used. This would increase the amount of blue light reflected, causing an underestimation of the amount of macular pigment present. An advantage of both methods is that a map of the amount of macular pigment is produced, not just a point estimate. Since macular degeneration involves the entire macula, knowledge of the topographical distribution of macular pigment would likely be more useful. On the other hand, these methods have a common disadvantage. Because two wavelengths are used, two different pictures need to be taken of the fundus. Even if these pictures are taken in close proximity to each other there is invariably movement of the eye and camera. This movement causes slight shifts in the field of view, magnification, and lighting of the fundus. It is possible to correct for these changes with the use of digital image processing software, but the corrections necessary take time, potentially introduce artifacts, and require specialized software.

TABLE I

REFERENCES

1 Bhosale P, Bernstein PS. Synergistic effects of zeaxanthin and its binding protein in the prevention of lipid membrane oxidation. Biochim Biophys Acta. 2005; 1740: 116-21.
2 Davies NP, Morland AB. Macular pigments: their characteristics and putative role. Prog Retin Eye Res. 2004; 23: 533-59.
3 Seddon JM, Ajani AU, Sperduto RD, et al. Dietary carotenoids, vitamins A, C, and E, and advanced age-related macular degeneration. Eye Disease Case-Control Study Group. JAMA 1994; 272: 1413-20.
4 Curran-Celentano J, Hammond BR Jr, Ciulla TA, et al. Relation between dietary intake, serum concentrations, and retinal concentrations of lutein and zeaxanthin in adults in a Midwest population. Am J Clin Nutr. 2001; 74: 796-802.

TABLE I-continued

REFERENCES

5 Hammond Jr., B. R., Fuld, K. and Curran-Celentano, J., 1995. Macular pigment density in monozygotic twins. Invest. Ophthalmol. Vis. Sci. 36, pp. 2531-2541.
6 Mares-Perlman JA, Brady WE, Klein R, Klein BE, Bowen P, Stacewicz-Sapuntzakis M, et al. Serum antioxidants and age-related macular degeneration in a population-based case control study. Arch Ophthalmol. 1995; 113: 1518-1523.
7 Mares-Perlman JA, Fisher AI, Klein R, Palta M, Block G, Millen AE, el al. Lutein and zeaxanthin in the diet and serum and their relation to age-related maculopathy in the third national health and nutrition examination survey. Am J Epidemiol 2001; 153: 424-32.
8 Dasch B, Fuhs A, Schmidt J, et al. Serum levels of macular carotenoids in relation to age-related maculopathy: the Muenster Aging and Retina Study (MARS). Graefes Arch Clin Exp Ophthalmol. 2005; 243: 1028-35.
9 Hammond Jr., B. R., Wooten, B. R. and Snodderly, D. M., 1996. Cigarette smoking and retinal carotenoids: implications for age-related macular degeneration. Vision Res. 36, pp. 3003-3009.
10 Hammond Jr., B. R., Ciulla, T. A. and Snodderly, D. M., 2002. Macular pigment density is reduced in obese subjects. Invest. Ophthalmol. Vis. 43, pp. 47-50.

SUMMARY OF THE INVENTION

The present invention overcomes a number of shortcomings of the prior art in measuring macular pigment by using a multispectral imaging technique that can provide such a measurement based on taking only a single image.

In one embodiment, a multiband filter is employed in combination with a color digital fundus camera. In that embodiment, the multiband filter has bandpass regions within spectral ranges of the red, green and blue detectors of the CCD array internal to the fundus camera, the bandpass regions being sufficiently sharply defined so as to avoid regions where the CCD detector responses spectrally overlap. This provides three discrete channels of grayscale data corresponding to the bandpass regions of the multiband filter, which can be used to calculate macular pigment topographically.

The invention also concerns the use of a system comprising, in one embodiment, a fundus camera having a CCD and a Bayer filter, a multiband filter, and a processor processing, storing, and displaying the resultant images, as more fully described in the detailed description.

Other features and advantages of the invention will be apparent from the description of the drawings and the detailed description which follow.

DETAILED DESCRIPTION

The following detailed description describes a number of preferred embodiments of various aspects of the invention. These embodiments are examples only of the full scope of what is enabled by this disclosure, and are not intended to limit the scope of the claims.

The present invention uses multispectral imaging, in which a plurality of light wavelengths are concurrently measured to obtain information about a target. In one embodiment, a reflectance method is used, in which multiband filters are used to simultaneously record specific wavelengths.

Multispectral imaging is commonly used in satellite imaging, but has not been widely applied to the eye. Often, multispectral imaging is accomplished by the use of multiple bandpass filters, with each selected bandwidth being imaged concurrently by different detectors. The use of multiple detectors would be difficult and expensive in clinical imaging of patients' eyes. Fundus cameras at one time used film for photographic documentation. With development of improved high resolution monochromatic charged coupled devices (CCDs), monochromatic film use was replaced with monochromatic digital imaging. It was common to use color slide film to record color images. Later development of sensitive, high-speed color digital cameras has led to the replacement of color film with electronic detectors in imaging the fundus.

Digital color cameras use monochromatic CCDs with a varying pattern of color filters in front of the individual elements of the CCD, so as to provide a color separation for the various monochromatic detectors. In this way, a plurality of grayscale channels can be output, each corresponding to one of the separated colors.

Figure 1:
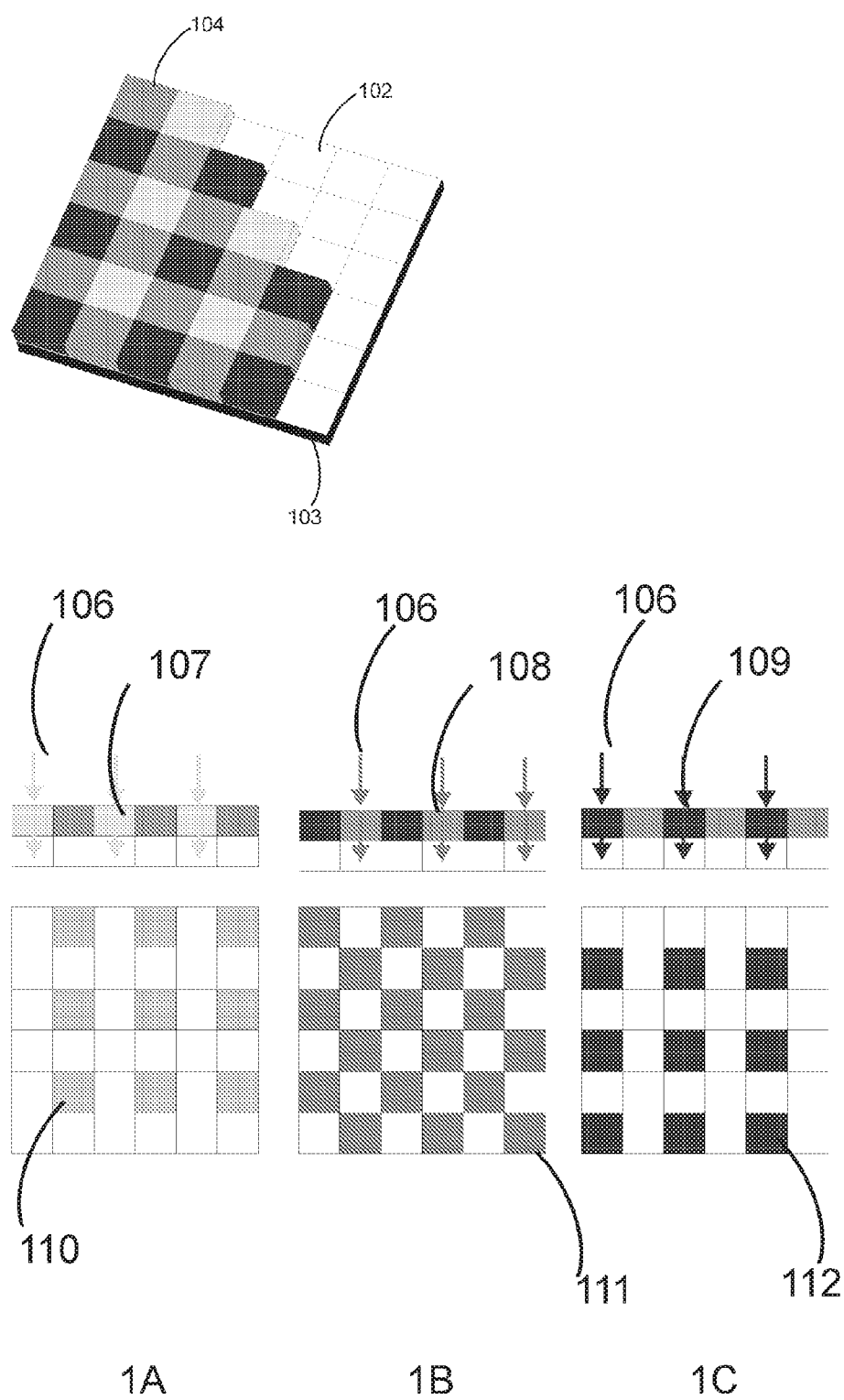
FIG. 1 shows a Bayer filter and a CCD as used in the prior art.

The most common method for using monochromatic CCDs in digital color cameras is to use a filter having a "Bayer" pattern (known as a "Bayer filter"). A schematic representation of a CCD with a Bayer filter is shown in FIG. 1. As shown in FIG. 1, the Bayer filter 104 is overlaid on CCD array 102 comprising individual monochromatic CCD elements 103 etc. The Bayer filter 104 has a checkerboard pattern of red, green, and blue filters, each positioned in front of a CCD element. The red, green and blue components, respectively, of incoming light 106 are passed by the respective red, green and blue filter elements 107, 108 and 109, to illuminate the respective underlying sets 110, 111 and 112 of CCD elements. Thus, the spectral sensitivity of each monochromatic CCD elements is modified by the filter element overlaying it. The three sets of CCD elements, 110, 111 and 112 produce three color-separated grayscale channels, 1A, 1B and 1C. By maintaining a representation of the coordinates of each CCD element in the outgoing signal, topographic, color-separated grayscale signals may be obtained in raster or other suitable form.

One problem, however, is that the color separation provided by the above-described arrangement is not very sharply defined. Since the design goal of a digital color camera is to produce accurate and pleasing color images, the red, green, and blue filters are not particularly specific and show significant overlap. Thus, the grayscale data obtained from a typical digital color camera is not sharply defined in the red, green and blue color ranges.

Figure 2:
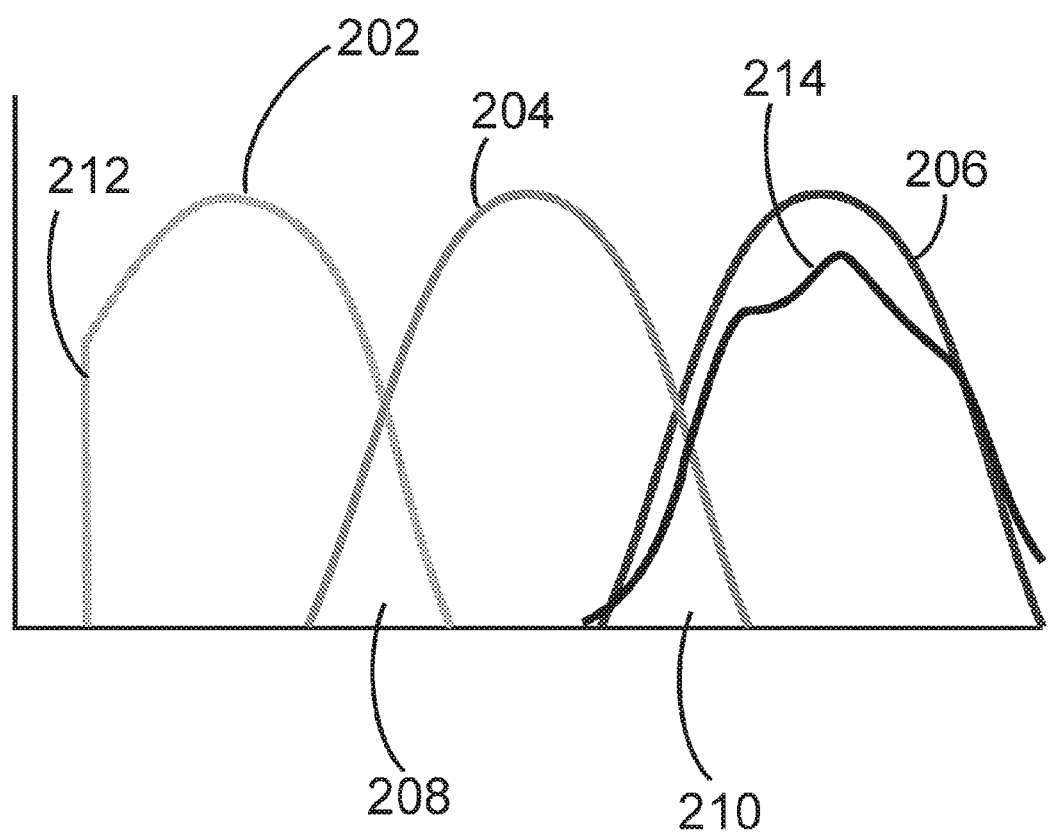
FIG. 2 shows an illustrative frequency response of a typical Bayer filter used in digital cameras.

The spectral characteristics of a typical digital color camera employing a CCD array with a Bayer filter is shown in curves 202, 204 and 206 of FIG. 2. It can be seen that there are significant spectral overlap regions between the Bayer filter elements, at 208 and 210. The absorption curve 214 for macular pigment is superimposed for comparison. As can be observed, while centered in the blue region 206, significant portions of this absorption curve also lies in the passband 204 of the green Bayer filter. This overlap would reduce the accuracy of any measurement of pigment by comparing grayscale images obtained from prior art instrumentation.

The present invention, in one embodiment, uses a multi-band filter to sharpen the color resolution of a digital color fundus camera. Using such a filter, it is possible to select red, green, or blue wavelengths and have the corresponding wavelengths imaged in the corresponding red, green, and blue channels of the color CCD. Such a method is particularly effective if the bandpass regions are selected so as to lie between and thereby avoid all or a substantial portion of the above-described spectral overlap areas between the filter responses of the Bayer filter within the camera's CCD. The result in such a case is to effectively sharpen the spectral response of the apparatus so that accurate measurements can be made.

Figure 3:
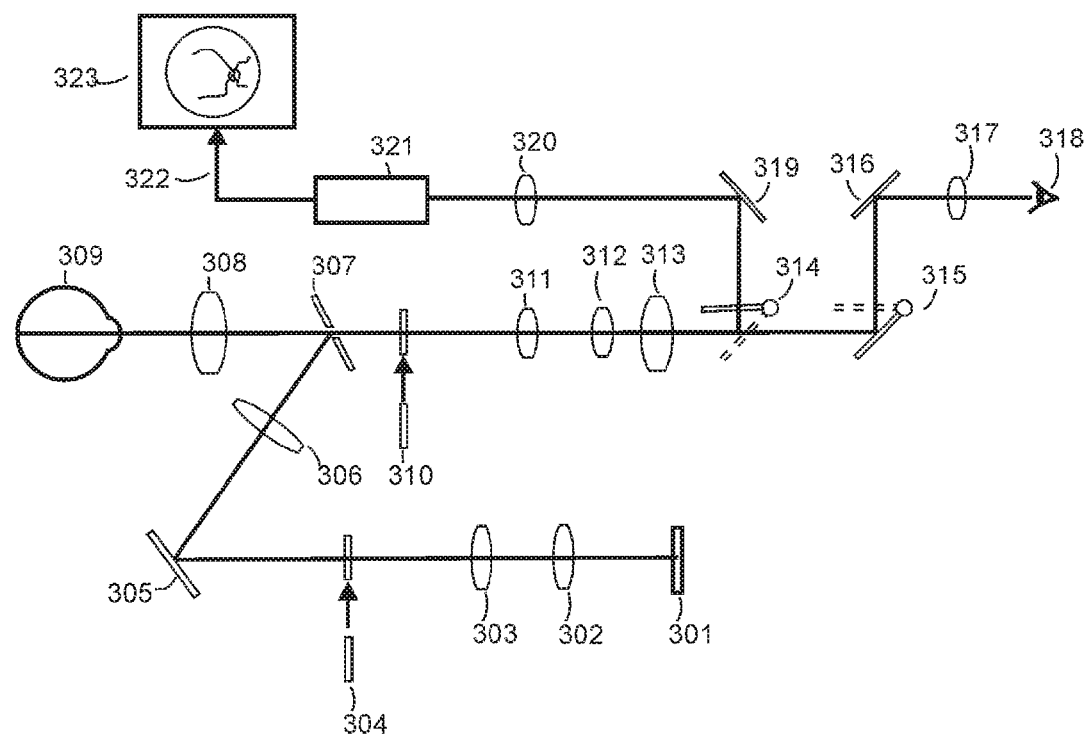
FIG. 3 is a simplified schematic diagram of a fundus camera-based system for macular imaging in accordance with the invention.

One embodiment of a fundus camera-based system for practicing the methods of the present invention is shown in FIG. 3. FIG. 3 is a simplified schematic diagram showing a fundus camera-based system for practicing the present invention, and an exemplary placement of the filters used for macular pigment imaging. In FIG. 3, 301 is the light source, which is generally a halogen light for viewing and a xenon flash lamp for photography. Light produced travels through condenser 302 and relay 303 lenses to reach the multiband passband filter at 304. This filter can be shifted into the optical path as need for macular pigment photography. The light is reflected by mirror 305 through relay lens 306 to the holed or fenestrated mirror 307. This directs light toward the eye through objective lens 308 into the eye 309. Light returning from the eye is focused by the objective lens through the hole in mirror 307. The barrier filter 310 is placed such that it can be brought into position to block unwanted wavelengths of returning light if needed. The light passes through focusing 311 and imaging lenses 312 and passes through the area occupied by a switching mirror 313. When the operator is viewing the fundus, light is directed to mirrors 314 and 315 through the eyepiece 16 to the operator's eye 317. When a photograph is taken the switching mirror position drops down and light is reflected to mirror 318 through relay lens 319 to the image-recording device 320. While this conceivably could be a film camera, in practical use it is a CCD camera connected electronically 321 to a computer and display 322. Images can be recorded digitally by frame capture.

Preferably, multiband filter 304 is a single filter having multiple optical bandpass regions. Such multiband bandpass filters are manufactured using ion beam sputtering and can obtain increased brightness and very accurate selection of bandpass wavelengths. These filters are commonly used for fluorescence microscopy. They are occasionally used for color photography. These filters can be designed to allow multiple bands of selected wavelengths to pass with blocking of unwanted wavelengths to equal or exceed 5 OD.

In the reflectance method used in one embodiment of the invention, multiband filters are used to record specific wavelengths simultaneously. The filter used for macular pigment imaging preferably has narrow bandpass regions near 465 nm, 535 nm, and 630 nm. These correspond to blue, green, and red visible wavelengths, and are represented in the blue, green, and red channels of the fundus camera, respectively. This allows simultaneous recording of three bands of information at no increase in cost for detectors. When combined, the resultant image is a full color image that looks remarkably like a regular color picture. The color information can be easily deconstructed into component channels. Since each of the separate channels was taken at the same time with the same camera and detector they have the same field of view, magnification, and lighting. This permits ratiometric evaluation without the need for any preliminary image registration steps.

Figure 4:
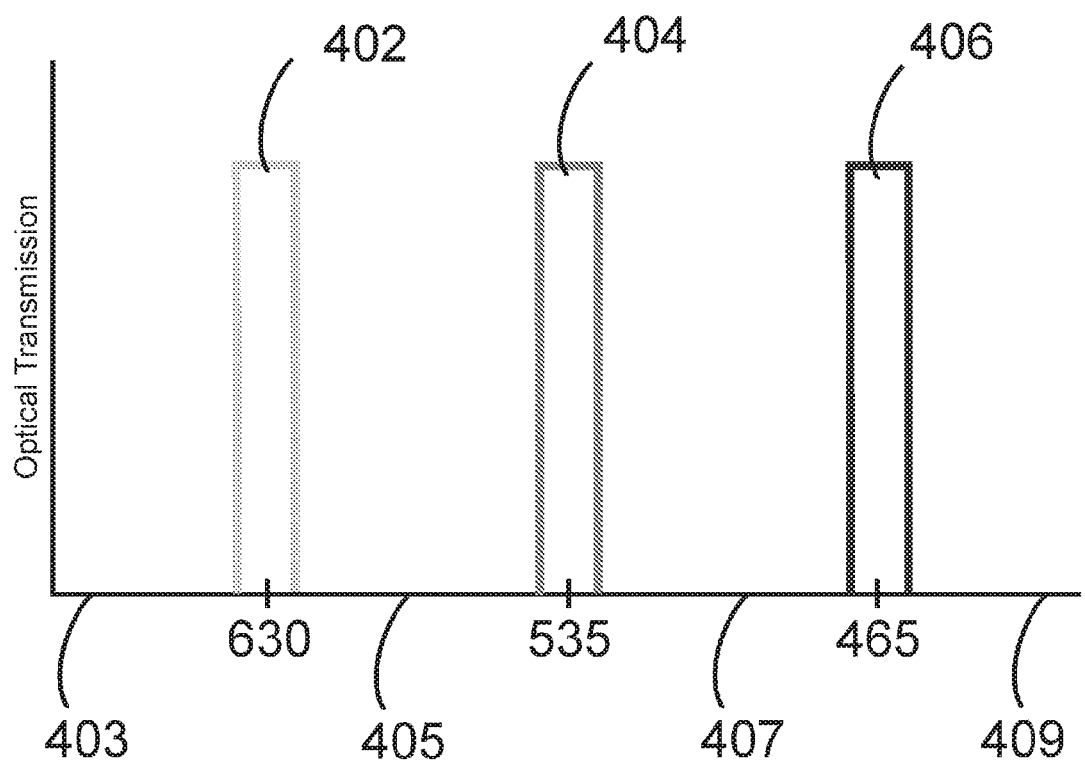
FIG. 4 shows the idealized frequency response of a multiband filter of one embodiment of the present invention.
Figure 5:
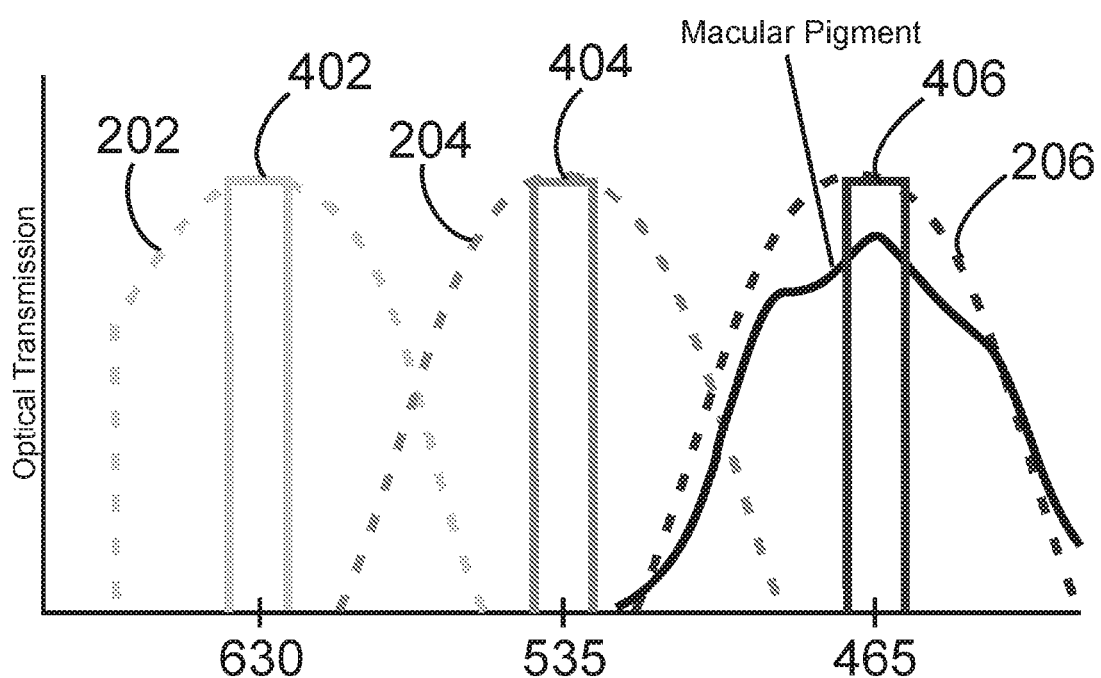
FIG. 5 shows a frequency response of a filter system where the multiband filter is coupled with a digital camera having a CCD with a Bayer filter.

FIG. 4 shows the idealized wavelength selection of the preferred embodiment multiband filter described above, with red green and blue bandpass regions 402, 404 and 406 respectively. FIG. 5 shows the filter bandpass regions of FIG. 4 overlayed on the spectral diagram of FIG. 2. It can be seen that in this representation, bandpass region 406 captures the (blue) peak of the macular pigment absorption curve 214, whereas bandpass region 404 captures a green signal including very little or none of the spectral region of macular pigment absorption.

To calculate the amount of macular pigment it is customary to calculate a ratio of the reflectance of the two wavelengths at two locations in the fundus, one within the region of the macula and the other in the periphery area outside of the region where there is deposition of the macular pigment. The optical density of the macular pigment is calculated as the $\log(\text{macula refl}\lambda_1/\text{macula refl}\lambda_2) - \log(\text{periphery refl}\lambda_1/\text{periphery refl}\lambda_2)$, where refl is the reflectance at either the long wavelength ($\lambda_1$) or the short wavelength ($\lambda_2$).

Figure 6:
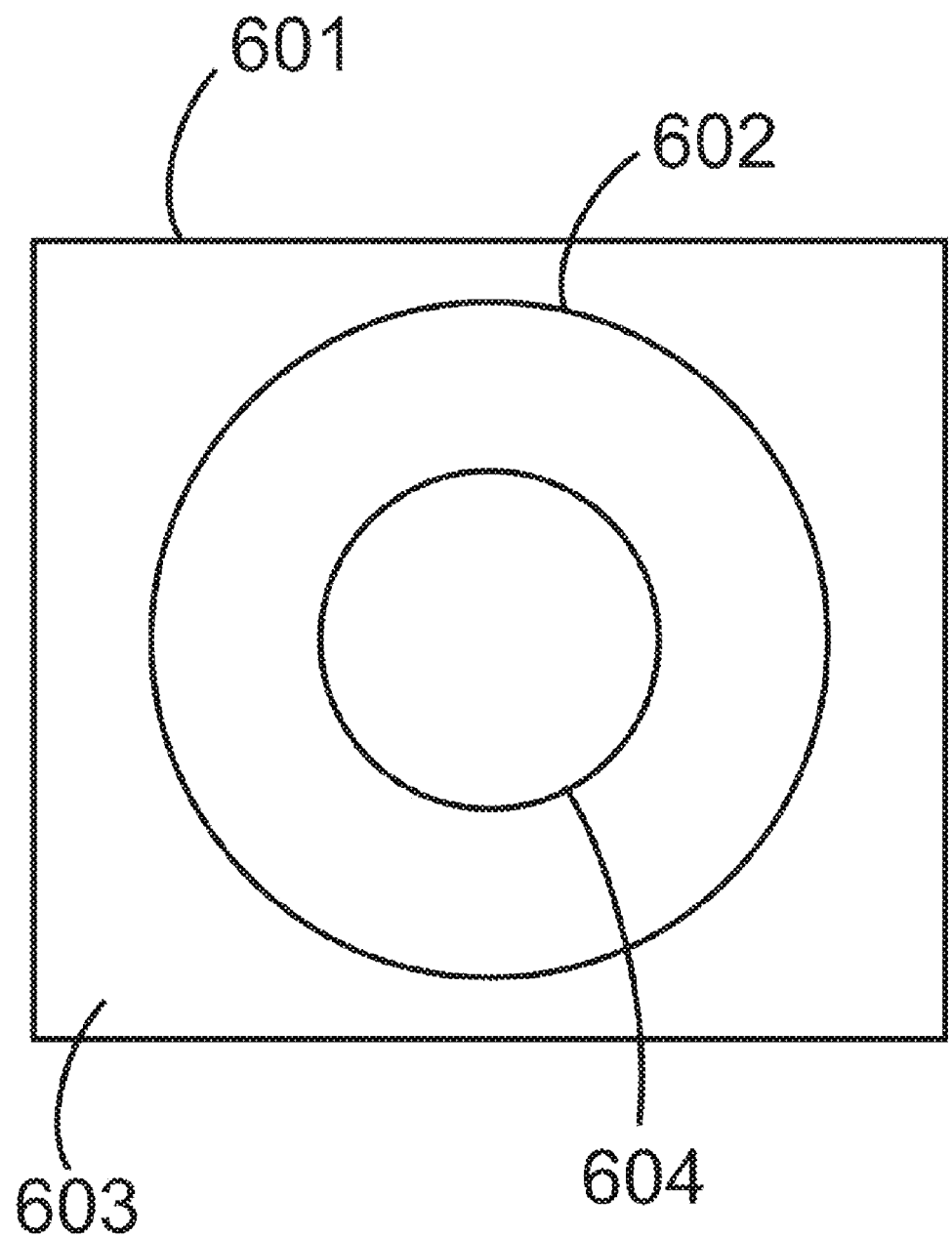
FIG. 6 is schematic representation of an image in accordance with the invention showing certain regions used for measurements and calculations.

The invention also concerns methods to display the spectral information. The typical fundus camera acquires a high resolution photograph of the eye that encompasses an angular measurement of approximately 50 degrees. The image may be acquired by a computer and processed digitally. Only the central portion of this is needed, and a rectangular area is selected. In one embodiment of the present system, as shown in FIG. 6, a rectangle 601 measuring 1640×1435 pixels per side is used which represents an area of approximately 8×7 mm. A circular region 602 in the central 1230 pixels is used to calculate the ratio macula $\text{refl}\lambda_1$/macula $\text{refl}\lambda_2$ and the remaining portion 603 of the rectangle is used to calculate periphery $\text{refl}\lambda_1$/periphery $\text{refl}\lambda_2$. The green channel information is divided by the blue channel. This produces a grayscale image where the macular pigment appears bright. However there may be a general level of gray visible outside of the region of interest caused by scatter, etc. The circular area 602, which corresponds to a 6 mm diameter circle centered on the posterior pole of the eye is measured within this square. The portion of the rectangle 603 not included in the central 6 mm circle is assumed to have negligible amounts of macular pigment. The mean grayscale level of this region is measured. This grayscale level is subtracted from the individual values of the pixels in the entire square. The resultant image has black regions where there is no macular pigment and varying levels of gray where there is pigment.

Figure 7:
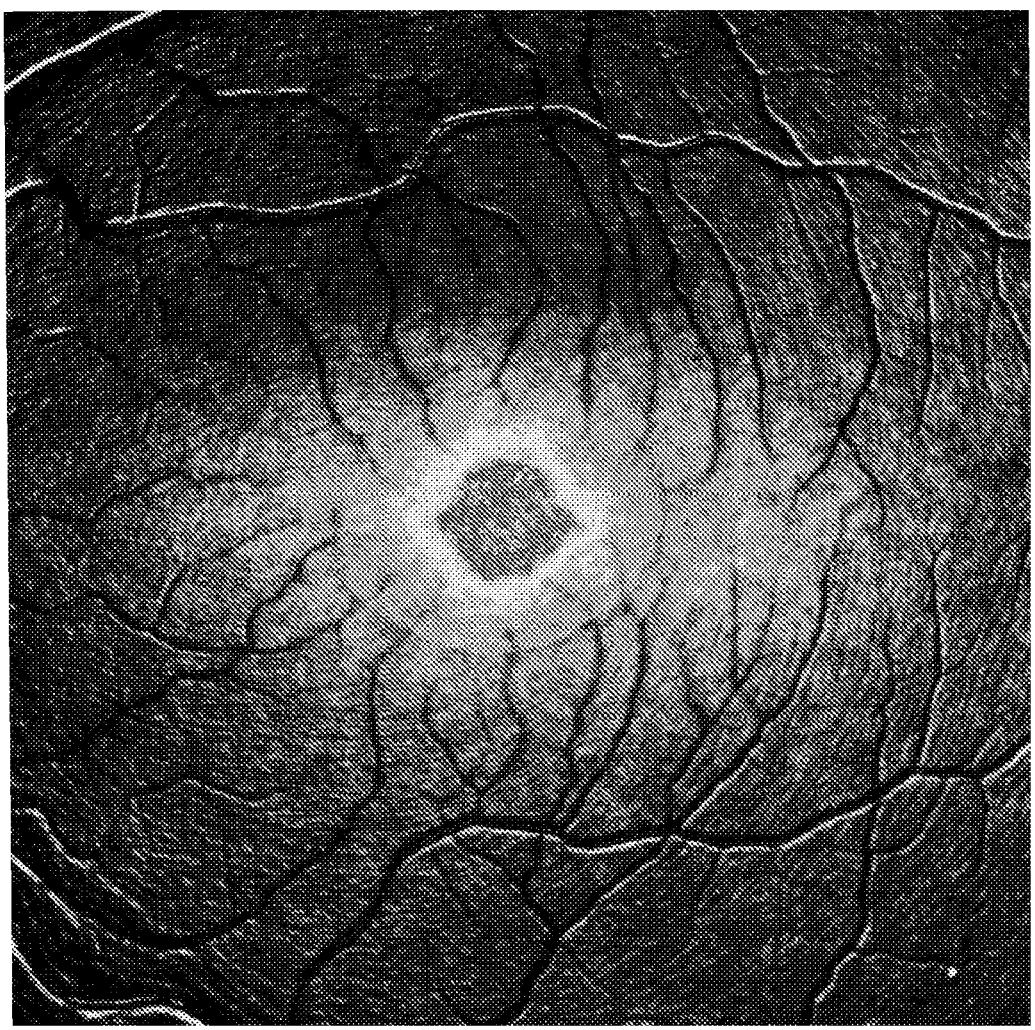
FIG. 7 is an example of a multispectral photograph taken with one embodiment of the present invention.

The human eye is not good at differentiating small changes in grayscale so, preferably, the images are given a pseudocolor. This helps differentiate small differences in the grayscale upon visual inspection. In one embodiment, as illustrated in FIG. 7, the pseudocolor is mapped to the grayscale by a method wherein the color assigned varies according to the underlying grayscale value, which in turn varies with the amount of macular pigment. The colors may be arranged in a gradient. In one embodiment, this gradient generally follows the order of the spectrum from red to violet, except that, because it is difficult to see the difference between blue, indigo and violet, the gradient was created such that the colors vary from black to blue for absent or nearly absent levels of pigment. Thus, the gradient map colors in that embodiment start at black and then range the colors of the rainbow from blue to green, yellow, orange and red, with white added to represent the greatest value, for increasing amounts of the underlying grayscale value. The mean value of the central 500 microns of the macula (604 in FIG. 6) is measured. This grayscale value is compared with a nomogram of values. The grayscale value of the person being tested is put into one of five groups based on the quintiles of normal distribution of the amounts of macular pigment in the general population. White is assigned to those in the highest quintile, red the second quintile, orange the middle quintile, yellow next, and green the lowest quintile. The rest of the pseudocolor map follows from the highest color down. This allows the examiner to rapidly estimate the amount of macular pigment present as compared with normative data.

In addition, each channel of output from the camera can be viewed in isolation to gain additional information about the ocular fundus. Alterations in the nerve fiber layer of the eye can often be best visualized by using short wavelengths of light as obtained with the blue portion of the filter. The green channel generally supplies the highest spatial resolution because there are more green sensitive elements in the color CCD. The red channel affords better visualization of deeper structures within the retina. Ratiometric comparisons between various channels, or composites of more than one channel can improve visualization as required. For example, an average of the red and green channels may be performed, and the average used to normalize the blue channel by dividing the blue channel with the red/green information, thereby improving contrast.

Accordingly, the present invention provides a multiwavelength, topographic analysis of macular pigment, acquired with a single photograph, using commonly available equipment and commercially obtainable filters, produces highly useful and accurate data regarding macular pigment, and provides representations of the data in forms most advantageous for visual inspection by the ophthalmologic practitioner.

It should be apparent from the foregoing, therefore, that the present invention achieves its objects and overcomes many of the shortcomings of the prior art.

Although the present invention has been described with specific embodiments, a variety of changes, substitutions, variations, alterations, and modifications in accordance with the principles and apparatus described herein may be readily suggested by this disclosure to one skilled in the art. It is intended that the invention encompass all such changes, substitutions, variations, alterations, and modifications as fall within the scope and spirit of the following claims.

I claim:
1. A method for imaging macular pigment in a patient comprising
   a) taking a digital color image of the macula using a digital color camera providing a plurality of discrete, color-associated gray-scale signals within a first set of color pass bands; and
   b) interposing in the light path of said camera at least one filter providing a second set of color pass band regions, wherein at least two of said second set of pass band regions are chosen to be within and narrower than two of the pass band regions of said first set of pass band regions, and one of said at least two of said second set of pass band regions is chosen to be approximately centered in the absorption band of macular pigment.

2. The method of claim 1 wherein said at least two of said second set of pass band regions each lies substantially outside of any area of spectral overlap between the respective pass band regions of said first set of pass bands.

3. The method of claim 1, wherein said digital color camera comprises an array of monochromatic light detectors and a filter array having individual filter elements corresponding to individual detector elements.

4. The method of claim 2 wherein said filter array is a Bayer filter and said at least one interposed filter is a multiband filter having bandpass regions centered near 465 nm, 535 nm, and 630 nm, and wherein each of said bandpass regions lies substantially outside of any area of spectral overlap between the respective pass band regions of said first set of pass bands of said filter array.

5. The method of claim 4 wherein said multiband filter comprises a single filter.

6. The method of claim 5 wherein said multiband filter is manufactured by ion sputtering.

7. The method of claim 1 further comprising performing an ophthalmologic analysis based upon said a visual representation of at least one of said grayscale signals.

8. The method of claim 7 wherein said analysis is based on a visual representation of a single one of said grayscale signals.

9. The method of claim 8 wherein said single grayscale signal corresponds to a blue pass band and said analysis comprises an analysis of nerve fiber.

10. The method of claim 8 wherein said single grayscale signal corresponds to a green pass band and said analysis comprises a spatial analysis.

11. The method of claim 8 wherein said single grayscale signal corresponds to a red pass band and said analysis comprises analysis of structures within the retina.

12. The method of claim 7 wherein said analysis is based on a visual representation derived from a calculation based on at least two of said grayscale signals.

13. The method of claim 12 further comprising averaging gray-scale signals corresponding to red and green pass bands and using said average to normalize a grayscale signal corresponding to a blue pass band by dividing the data from said blue pass band by said red/green average data thereby improving the contrast provided by said blue pass band data.

14. A method for measuring macular pigment comprising
   a) performing the method of claim 1 and obtaining in connection therewith, grayscale data from said grayscale signals, at least two wavelengths A1 and A2, the second of which wavelengths being approximately centered in the absorption band of macular pigment and the first of said at least two wavelengths being a longer wavelength in the green portion of the spectrum;

b) calculating the ratio of the reflectance of said two wavelengths at first and second locations in the fundus, the first location (macula) being within the region of the macula and the second location (periphery) being outside of the region where there is deposition of the macular pigment; and c) calculating the optical density of the macular pigment as the log(macula refl A1/macula refl A2)−log(periphery refl A1/periphery reflA2), where refl A1 is the reflectance at the longer wave-length (A1) and refl A2 is reflectance at the shorter wavelength (A2), at the macula and periphery locations, respectively.

15. The method of claim 14 used to create a grayscale image by a series of steps further comprising a) selecting a generally rectangular area of said image, corresponding to an area of approximately 8×7 mm of the ocular fundus enclosing the macula;

b) selecting a generally circular region of approximately 6 mm diameter approximately centered in said generally rectangular area;

c) designating said generally circular area as said first (macula) location; and d) designating the portion of said generally rectangular area outside of said generally circular area as said second (periphery) location.

16. The method of claim 15 further comprising subtracting the mean grayscale value measured in said generally rectangular area outside of said generally circular area from the grayscale values measured at each point throughout said generally rectangular area.

17. The method of claim 16 adapted to create a pseudocolor image by a series of steps further comprising assigning visual indicia selected from a set of visual indicia to a set of grayscale values in an image and displaying said visual indicia at the locations of the corresponding grayscale values in accordance with said selection of visual indicia.

18. The method of claim 17 wherein said visual indicia are colors.

19. The method of claim 18 wherein said colors are assigned from a set of colors regarded as ordered in a gradient and wherein each of said colors is assigned to grayscale values in accordance with the position of the respective ones of said colors in said gradient.

20. The method of claim 19 wherein said gradient ranges from black to blue for grayscale values corresponding to absent or nearly absent levels of macular pigment, and ranges over other colors for increasing amounts of the underlying grayscale value.

21. The method of claim 20 wherein said other colors range from green, yellow, orange, red, and then white for increasing amounts of the underlying grayscale value.

22. The method of claim 19 further comprising normalizing said image with respect to a generally representative set of subjects by a series of steps further comprising a) measuring the mean grayscale value of approximately the central 500 microns of the macula:

b) comparing said grayscale value with a nomogram of corresponding values measured from a generally representative set of subjects and assigning said grayscale value to a group based on its position with respect to said nomogram;

c) selecting the color to represent the highest grayscale value in said image in accordance with said assigned group; and d) scaling the selection of the other colors in said color gradient according to said highest color value.

23. The method of claim 22 wherein the grayscale value of the person being tested is put into one of five groups based on the quintiles of normal distribution of the amounts of macular pigment in the general population, and wherein white is assigned to represent the highest grayscale value for those in the highest quintile, red for the second quintile, orange for the middle quintile, yellow next, and green for the lowest quintile, and the remainder of the color map for said psuedocolor image follows from said assigned color in accordance with a color gradient wherein the respective colors representing the highest level of macular pigment to an absent level of macular pigment range from white to red to orange to yellow to green to blue to black.

* * * * *